United States Patent [19]

Kloepper

[11] Patent Number: 4,854,313
[45] Date of Patent: Aug. 8, 1989

[54] SURGICAL LEG STRESSING DEVICE

[76] Inventor: Paul A. Kloepper, 2014 Robin Hill La., Carrollton, Tex. 75010

[21] Appl. No.: 887,177

[22] Filed: Jul. 16, 1986

[51] Int. Cl.[4] .............................................. A61F 13/00
[52] U.S. Cl. .................................... 128/882; 294/156
[58] Field of Search ...................... 128/83.5, 84 R, 85, 128/87 R, 94, 133, 165, 166, 83, 83 R, 75; 5/443; 294/140, 152, 153, 156; 383/6, 31

[56] References Cited

U.S. PATENT DOCUMENTS

| 2,053,753 | 9/1936 | Wellington | 128/84 R |
|---|---|---|---|
| 2,088,927 | 8/1937 | Roy | 128/94 |
| 2,605,945 | 8/1952 | Dechar | 294/152 |
| 2,722,692 | 11/1955 | Dempster | 128/83 |
| 2,936,927 | 5/1960 | Peters | 294/167 |
| 3,827,614 | 8/1974 | Baxter et al. | 294/156 |
| 3,957,041 | 5/1976 | Wilder | 128/84 R |
| 4,402,542 | 9/1983 | Kreutzer | 294/156 |

Primary Examiner—Richard J. Johnson
Assistant Examiner—Charles H. Sam

[57] ABSTRACT

A surgical accessory for imposing a controlled and appropriate stress to a surgical joint during arthroscopic surgery. The device is comprised of a substantially inelastic composition defining a sling adapted to be positioned about a selected location of the limb displaced from the joint on which surgery is to be conducted. A transverse handle is secured to the sling and enables the sling to be hand held and carefully manipulated to impose the required stress from the limb location to the joint. The device can be advantageously utilized during arthroscopic surgery of the knee joint. In one embodiment the sling is slit to embrace the ankle with the heel protruding through the slit. In a second embodiment, the sling is comprised of two juxtaposed sections at least one of which is adjustable. Forces provided to the handle by the holder of the device are transmitted from the handle to the sling for appropriate positioning of the ankel whereby proper stressing of the knee joint is achieved.

12 Claims, 2 Drawing Sheets

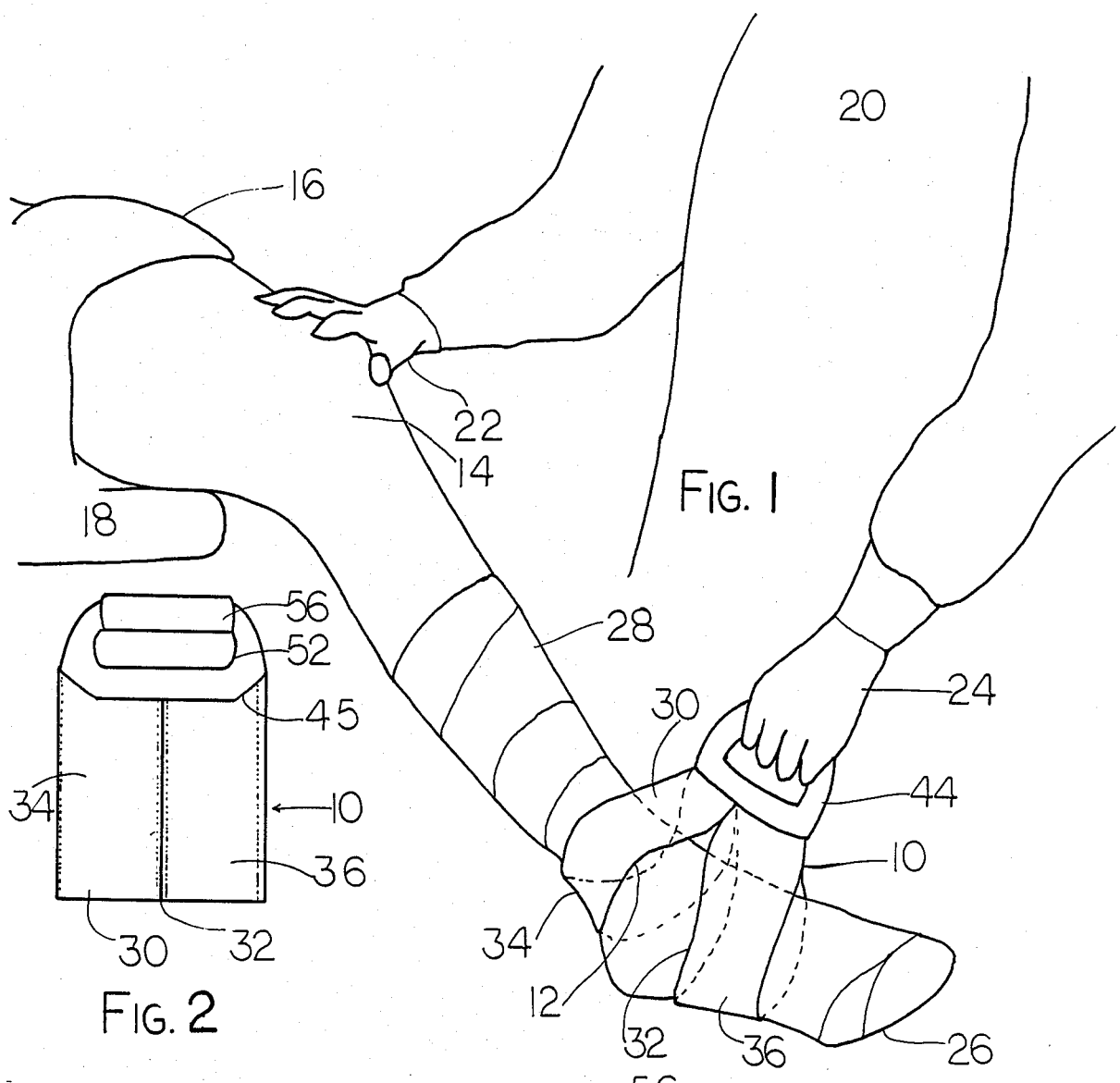
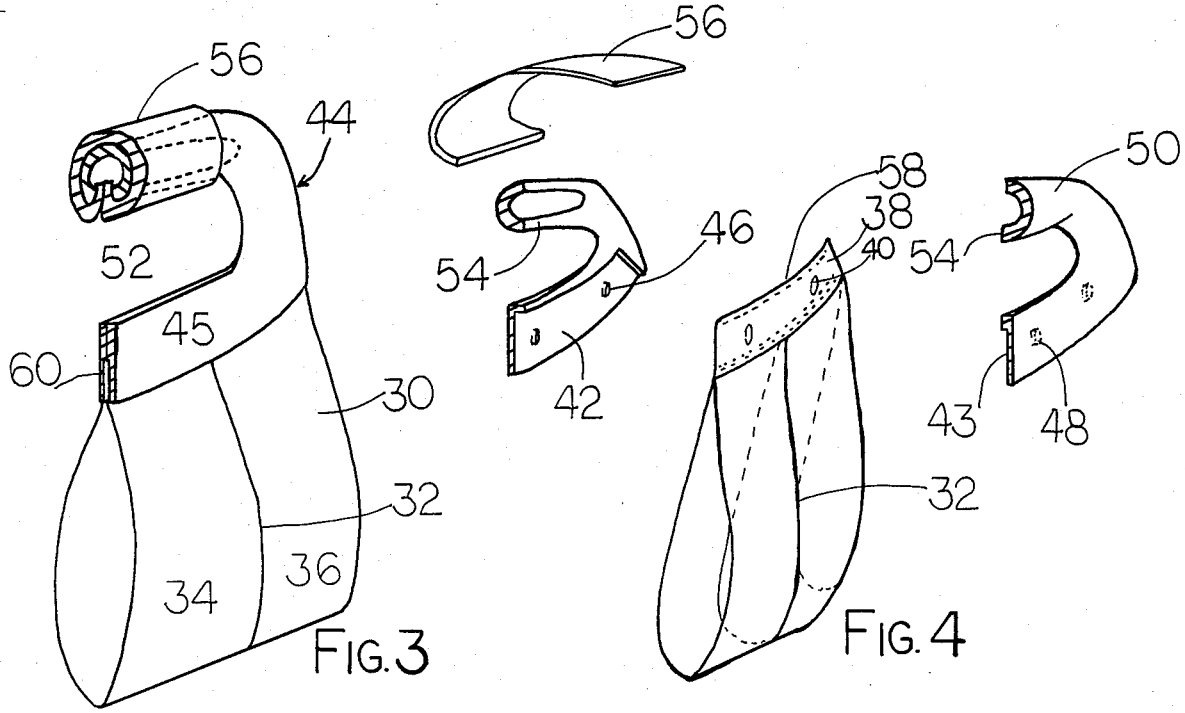

SURGICAL LEG STRESSING DEVICE

TECHNICAL FIELD

The field of art to which the invention pertains comprises the field of medical surgery and more specifically to accessories for limb support during arthroscopic surgery.

BACKGROUND OF THE INVENTION

Knee joint surgery and the diagnosis of knee injuries are increasingly being conducted by the use of arthroscopic surgery. After making the incision, the surgeon utilizes an arthroscope whereby derangement disorders can be more readily determined. The arthroscope is an instrument utilizing fiberoptics capable of providing extremely close and view enlarged inspection of the affected joint area. The images are projected onto a television screen which is continuously observed by the surgeon as surgery is being performed. Various devices are known for partially supporting the limb during the conduct of arthroscopic surgery as for example disclosed in U.S. Pat. Nos. 4,299,213 and 4,549,540.

In addition to the partial support for the limb provided by such prior art devices, arthroscopic surgery requires that a controlled stress be imposed on the joint to aid the surgeon in viewing and gaining access to the affected joint area. The precise form of stress to be applied varies both by type and degree during the course of the surgery and typically comprises a valgus lateral stress or a varus medial stress along with various flexion/extension of the knee. Imposing such stresses requires not only medical knowledge of the procedure but is of course very delicate and requires that it ,be carefully and accurately applied. Failure to apply the required stress at the appropriate time and to the required degree can introduce serious compromises in the access, visualization, diagnosis and subsequent surgical treatment of the occult disorder.

Current procedures for imposing such stress to, for example the knee joint, are effected by a medical assistant or aide holding the foot or ankle in his or her gloved hands in an otherwise unsupported and relatively elevated position. This enables the foot or ankle to be manipulated at will whereby any movement will be transmitted as an appropriate stress imposed on the knee joint. It will be appreciated that the stress provider in order to utilize both hands while delivering the stress is usually unable to stand erect but must instead be bent or slumped with the leg weight and positioning literally resting in his hands. Consequently the present hand held manipulation of the foot or ankle for those purposes has proved awkward due to fatigue of the provider thereof especially with a larger patient whose legs are heavier than average. Indeed, this problem is exasperated by a loose, non-adherent stockinette which is frequently slipped over the leg for purposes of sterility and secured with a coban wrap. Marked slippage at the stockinette interface frequently occurs with a resulting loss of optimal stress and leg position. Additionally, hand gripping of a foot often causes the undesirable effect of compressing the posterior tibial neurovascular bundle.

Despite recognition of the foregoing, a ready solution therefor has not heretofore been known.

SUMMARY OF THE INVENTION

The present invention relates to surgical accessories. More specifically, the invention relates to a hand held device for the timely imposition of a controlled and appropriately directed stress to the surgical joint during arthroscopic surgery without the need to hand grip the ankle or other selected location displaced from the joint in the manner of the prior art. This is achieved in accordance with the device of invention which is comprised of an inelastic sling that encompasses the ankle or other selected location. The device is hand held with one hand to support the limb elevated thereat while enabling the holder to stand fully erect at all times. For holding the device there is provided a relatively rigid plastic gripping handle that is comfortably padded and easily manipulated by the medical assistant or aide in providing the carefully controlled imposition of the stress being applied. By means of the device hereof, the knee or other joint being subjected to surgery can be continuously stressed without hand slippage, even during prolonged surgical procedures and without adversely affecting the neurovascular bundle in the foot areas.

The advantages afforded thereby are numerous not least of which is the relief of tension and fatigue factors attributed to the provider of the stress service. Consequently, this enables the specific type and degree of stress to be more carefully and consistently imposed and varied during the prolonged course of the surgical procedure.

It is therefore an object of the invention to provide a novel device for the imposition of joint stress during the course of arthroscopic surgery.

It is a further object of the invention to effect the last recited object with a device that is easily and simply manipulated for imposing the required type and degree of stress thereto as needed.

The above noted features and advantages of the invention as well as other superior aspects thereof will be further appreciated by those skilled in the art upon reading the detailed description which follows in conjunction with the drawing.

BRIEF DESCRIPTION OF THE DRAWINGS

FIG. 1 is a perspective view illustrating the device of the invention in accordance with a first embodiment being utilized to impose a varus stress to the right knee of a patient;

FIG. 2 is a front elevation of the device of FIG. 1;

FIG. 3 is a fragmentary sectional perspective of the device of the FIG. 1;

FIG. 4 is an exploded partially sectioned perspective of the component elements of the device of FIG. 1;

DESCRIPTION OF THE PREFERRED EMBODIMENT

Figure 5:
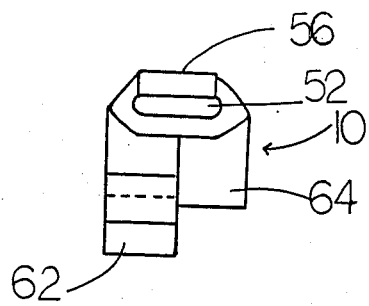
FIG. 5 is a front elevation of the device of the invention in accordance with a second embodiment.

In the description which follows, like parts are marked throughout the specification and drawing with the same reference numerals respectively. Drawing figures are not necessarily to scale and in certain views parts may be drawn rotated into the plane of the drawing for purposes of clarity.

Referring now to the drawings, the stress device in accordance herewith is designated 10. As shown in FIG. 1, the device is being hand held by the user thereof designated 20 to manipulate the ankle 12 and impose a varus stress on the knee joint 14 of the patient 16 lying on operating table 18. The medical assistant standing erect has his right hand 22 on the thigh in order to stabilize the knee while his left hand 24 is holding support device 10 and pulling medially on the leg. The foot, ankle and lower leg have been wrapped for purposes of sterility in a loose stockinette 26 overlaid with a coban tape 28.

Comprising stress support device 10 in accordance with the first embodiment hereof is a sling 30 formed of a soft, but strong and inelastic fabric which in preferred embodiment comprises a polyester synthetic nonwoven material such as marketed by DuPont under the trademark SONTARA. A vertical slit 32 extending from an underside intermediate location thereof enables a spreading of the fabric in the manner of FIG. 1 for allowing the patient's heel to protrude outwardly between the separate straplike sling sections 34 and 36.

To form the sling formation, a controlled length of fabric is folded over and the loose ends are secured together via a stitched seam 58 to a reinforcing flap 38 containing spaced apart apertures 40. Support of the sling is provided by a transverse handle 44 that includes separate and complementary sections 42 and 43. Handle section 42 includes dowels 46 in the lower bar 45 thereof while section 43 includes apertures 48 in which the dowels are received in an assembled press fit relation. The dowels when assembled extend through sling apertures 40 while a recess 60 defined between sections 42 and 43 enables the sling flap to be received and secured in a sandwiched relation.

The lower bar 45 of handle 44 is merged in a looping arrangement with a gripping handle 50 so as to define a finger space 52 therebetween. The gripping handle, as best seen in FIGS. 3 and 4, is comprised of an elongated tubular handle of polymer plastic composition which along its underside defines an elongated longitudinal slot 54. Received and secured within slot 54 are the opposed ends of a relatively soft wrap 56 which in a preferred embodiment is comprised of an adherent closed cell polyethylene foam composition marketed by the Minnesota Mining and Manufacturing Company. The wrap affords significant added comfort to the hand 24 of the user 20 without detracting from the stress service he is to provide.

For securing flap 38, a suitable adhesive is initially applied to the opposing surfaces of the recess 60 of the handle. The flap is then positioned in the recess with apertures 40 in receipt of dowels 46. Wrap foam 56 is similarly secured adhesively about gripping handle 50 and the ends folded inwardly to within the handle spacing defining slot 54.

Once assembled, the finished product is packaged, sterilized, and ready for use in a sterile operating room when the occasion arises. Use of the device is relatively simple in that the sling is readily slipped over the foot whereby the separable components 34 and 36 embrace the heel in the manner illustrated in FIG. 1. By grasping gripping handle 50, positioning of the foot relative to the knee joint in order to impose a controlled stress thereon is readily and easily effected by appropriate hand movement of the handle 44.

Figure 6:
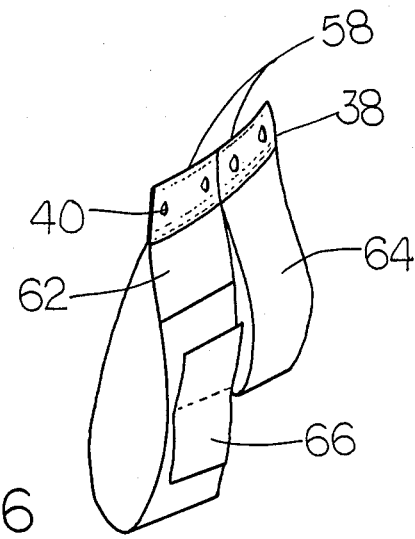
FIG. 6 is a partial perspective view of the device of FIG. 5.
Figure 7:
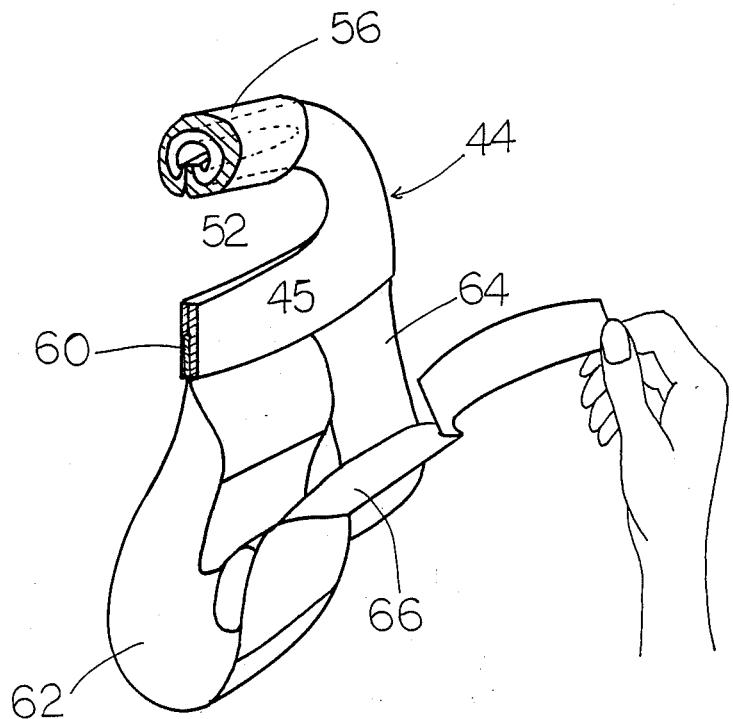
FIG. 7 is a fragmentary sectional perspective of the device of FIG. 5.

The second embodiment of the invention will now be described with specific reference to FIGS. 5-7. For this embodiment, the device 10 is comprised of two individual strap like sling sections 62 and 64. Section 62 is longer and adjustable as compared to section 64 which is relatively shorter and non-adjustable. As will be appreciated from the discussion below, this embodiment enables both a sliponmounting on to the limb as before while also affording a degree of flexibility in custom sizing the device about the limb area to be manipulated.

To achieve the foregoing, each section 62, 64 is separately formed with a flap 38 and stitching 58. Each flap includes two apertures 40 through which to receive a corresponding number of dowels 46. Both sections 64 and 62 are of a continuous uninterrupted length joined at a flap 38 while longer section 62, unlike section 64 is adapted to be effectively shortened by a suitable attachment 66. Attachment 66 could, for example, be a sewn on adhesive backed tape with a detachable protective liner 68. Removal of the liner enables the tape to be applied elsewhere to an upper portion of the sling or to the side face of handle 44 as appropriate to effect the required degree of sling shortening. Where reuse or readjustment of the device is contemplated, attachment 66 can comprise reusable hook and loop type materials marketed commercially under the trademark Velcro.

By the above description there is disclosed a novel accessory for limb support during the course of arthroscopic surgery whereby appropriate stress can be timely and controllably applied without the attendant disadvantages associated with applying such stresses two handedly in the manner of the prior art. The support unit is relatively simple and uncostly to manufacture, yet provides a magnificent improvement in enabling the surgeon to more readily concentrate on the surgical area without the distractions associated with maintaining the optimal stress at the joint. Being that the stress can be imposed with one hand while the provider thereof is able to stand erect, the fatigue factors associated with the bent over two hand holding of the foot in accordance with existing practice is largely eliminated. At the same time, control over foot movement is substantially enhanced by virtue of the inelastic properties of the fabric. Moreover, the undesirable pressure previously applied to the posterior tibial neurovascular bundle is totally eliminated. While the above has been described principally in connection with performing arthroscopic surgery on knee joints, it is similarly adaptable for supporting a limb during arthroscopic joint surgery of the ankle, arm, shoulder, etc.

Since many changes could be made in the above construction and many apparently widely different embodiments of this invention could be made without departing from the scope thereof, it is intended that all matter contained in the drawings and specification shall be interpreted as illustrative and not in a limiting sense.

I claim:

1. Apparatus for providing controlled stress support for a limb having a joint on which arthroscopic surgery is to be performed and comprising in combination:
   (a) a sling of substantially inelastic fabric composition adapted to be positioned about a selected location of the limb displaced from the joint on which surgery is to be conducted, said sling being comprised of two juxtaposed sections at least one of which is adjustable for changing the length thereof relative to the other section whereby to conform each section to the limb location on which it is to be positioned; and
   (b) handle means secured transversely to an upper portion of said sling enabling the sling to be hand held and manipulated while the limb is elevated to impose a required stress on the joint during the course of the surgery.

2. Apparatus in accordance with claim 1 in which said sling where secured to said handle means is comprised of opposed layers of said fabric secured along a common edge by a reinforcing flap means and said common edge and said flap means are secured to said handle means.

3. Apparatus in accordance with claim 2 in which said handle means is comprised of complementary interfitting sections including fastener means extending between said sections and through apertures in said flap means for securing said flap means to said handle means.

4. Apparatus in accordance with claim 3 in which said handle means includes a recess defined intervening between said complementary sections and said flap means is secured in a sandwich relation in said recess.

5. Apparatus in accordance with claim 4 in which said sling includes an intermediate slit adapted to cause fabric separation thereat for embracing the selected location of the elevated limb.

6. Apparatus in accordance with claim 5 in which the joint on which arthroscopic surgery is to be conducted comprises the knee and said selected location that said sling is adapted to embrace comprises the ankle.

7. Apparatus according to claim 1 including attachment means capable of being selectively applied to effect a shortening adjustment of the adjustable of said sections.

8. Apparatus according to claim 7 in which said attachment means comprises an adhesive backed tape.

9. Apparatus in accordance with claim 5 in which said handle means is of a polymer plastic composition and includes a tubular gripping portion and an elastomeric wrap secured about the gripping surface of said gripping portion to aid in the holder comfort during the conduct of surgery.

10. Apparatus in accordance with claim 9 in which said wrap terminates inwardly of the gripper portion of said handle means secured between the complementary sections thereof.

11. Apparatus in accordance with claim 1 in which said handle means is of a polymer plastic composition and includes a tubular gripping portion and an elastomeric wrap secured about the gripping surface of said gripping portion to aid in the holder comfort during the conduct of surgery.

12. Apparatus in accordance with claim 11 in which said wrap terminates inwardly of the gripper portion of said handle means secured between the complementary sections thereof.

* * * * *